(12) United States Patent
Niblock et al.

(10) Patent No.: US 8,328,560 B2
(45) Date of Patent: Dec. 11, 2012

(54) LAPAROSCOPIC APPARATUS

(75) Inventors: Ian Niblock, Belfast (GB); Robert Bailie, Helen's Bay (GB); Walter Prendiville, Rathcoole (IE); Ray O'Sullivan, Kilkenny (IE)

(73) Assignee: Endosim Limited, Belfast (GB)

( * ) Notice: Subject to any disclaimer, the term of this patent is extended or adjusted under 35 U.S.C. 154(b) by 1042 days.

(21) Appl. No.: 12/327,604

(22) Filed: Dec. 3, 2008

(65) Prior Publication Data

US 2009/0176196 A1 Jul. 9, 2009

(30) Foreign Application Priority Data

Dec. 3, 2007 (EP) .................................... 07023329

(51) Int. Cl.
*G09B 23/28* (2006.01)
(52) U.S. Cl. ...................................................... 434/262
(58) Field of Classification Search .................. 434/55, 434/57, 58, 61, 62, 63, 67, 262, 272
See application file for complete search history.

(56) References Cited

U.S. PATENT DOCUMENTS

| | | | | |
|---|---|---|---|---|
| 5,403,191 A | * | 4/1995 | Tuason | 434/262 |
| 5,425,644 A | * | 6/1995 | Szinicz | 434/268 |
| 5,947,743 A | * | 9/1999 | Hasson | 434/262 |
| 6,024,576 A | * | 2/2000 | Bevirt et al. | 434/262 |
| 6,377,011 B1 | | 4/2002 | Ben-Ur | |
| 6,659,776 B1 | | 12/2003 | Aumann et al. | |
| 8,007,281 B2 | * | 8/2011 | Toly | 434/262 |
| 2004/0024418 A1 | | 2/2004 | Irion et al. | |
| 2005/0142525 A1 | * | 6/2005 | Cotin et al. | 434/262 |
| 2007/0172803 A1 | * | 7/2007 | Hannaford et al. | 434/262 |
| 2010/0273134 A1 | * | 10/2010 | Chen | 434/262 |

FOREIGN PATENT DOCUMENTS

DE 10304736 B3 9/2004

* cited by examiner

*Primary Examiner* — Kurt Fernstrom
(74) *Attorney, Agent, or Firm* — Christopher & Weisberg, P.A.

(57) ABSTRACT

The present invention relates to a laparoscopic apparatus. In particular, it relates to an apparatus for the training of medical professionals, particularly those engaged in the field of laparoscopic surgery. The apparatus comprises a housing; an opening in the housing through which a laparoscopic tool can pass; retaining means in operative association with the opening and adapted to guide the laparoscopic tool through the opening, the retaining means providing resistance to movement of the laparoscopic tool. Accordingly, the present invention provides a realistic surgical experience by mimicking the sensation of carrying out surgical techniques on a patient.

15 Claims, 7 Drawing Sheets

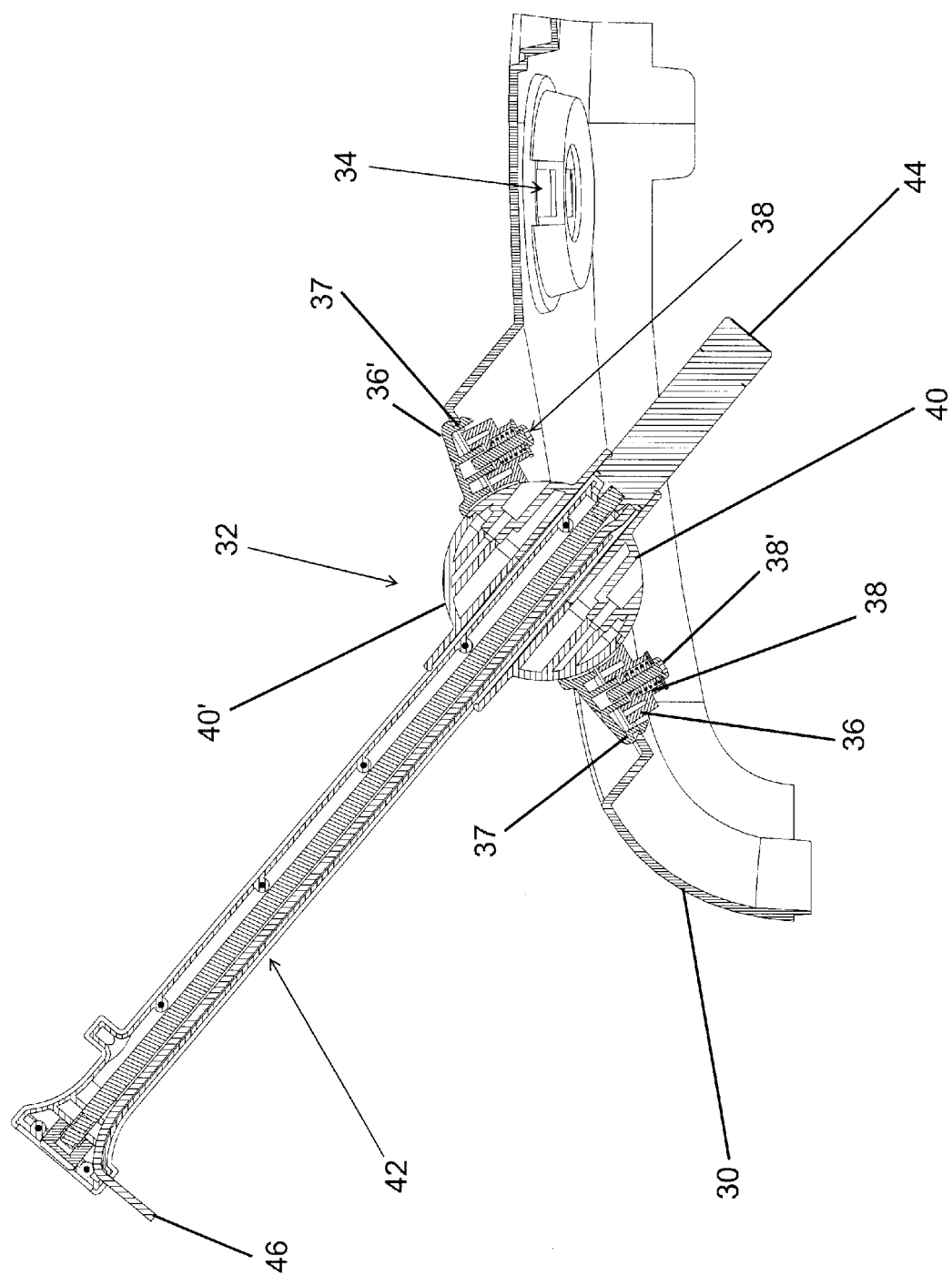

LAPAROSCOPIC APPARATUS

CROSS-REFERENCE TO RELATED APPLICATION

This application is claims priority to European Patent Application No. 07023329.1 filed Dec. 3, 2007, entitled LAPAROSCOPIC APPARATUS, the entirety of which is incorporated herein by reference.

FIELD OF THE INVENTION

The present invention relates to a laparoscopic apparatus. In particular, the invention finds utility as a training apparatus for laparoscopic surgery techniques.

BACKGROUND

Laparoscopic surgery is a modern surgical technique performed through small incisions, which involves the visualisation of body cavities using telescopes with attached camera systems. Trocars or cannulae are inserted through the incisions to facilitate the smooth passage of telescopes and slender long instruments into these cavities. A fundamental feature of laparoscopic surgery is the use of a laparoscope: a telescopic rod lens system that is usually connected to a visual acquisition device, such as a camera. Most typically, a fibre optic cable system connected to a 'cold' light source such as halogen or xenon is used to illuminate the operative field. The internal appearances of the body cavities are visualised on visual display monitors. The monitor image is 2-dimensional, and the movement of the instruments is seen in parallax. These combined features mean that surgeons training in this field of surgery not only have to learn individual surgical procedures, they must also become comfortable working in a 3-dimensional environment which has been translated to a 2-dimensional output.

The restricted vision, the difficulty in handling of the instruments, the acquisition of new hand-eye coordination skills, the lack of tactile perception and the limited working area are factors which add to the technical complexity of this surgical approach. For these reasons, minimally invasive surgery has emerged as a highly competitive new sub-specialty within various fields of surgery. Surgical residents, who wish to focus on this area of surgery, gain additional training during one or two years of fellowship after completing their basic surgical residency. Accordingly, the use of a simulator allows the trainee surgeon not only to learn the skills that when eventually combined, become a procedure, but they can also experience the unique appreciation of 2-dimensional visualisation of the 3-dimensional surgical field.

A simulator replicating the laparoscopic environment as experienced in an operating theatre, is superior to other inanimate simulators. Any learned procedure is a combination of several different skills, in other words all procedures can be broken down into individual component skills. These skills include the ability to correctly orientate a camera, manipulate objects in 3 dimensions, cut tissue, and suture (stitch). The simulator facilitates the trainee in attaining proficiency at these tasks prior to actually entering the operating room environment.

Once a surgical trainee or surgeon acquires a skills set, they can then move on to performing a variety of surgical procedures. It is estimated that individual skills have to be repeated up to 30 times before a surgeon is considered proficient. This also applies to entire procedures. A simulator can also help simulate an entire procedure, where the skills are combined on a suitable model, again without endangering a patient. For example a laparoscopic cholecystectomy (removal of a gall bladder), the most common laparoscopic procedure performed, is a combination of grasping, dissection, clipping and cutting. All these skills can be simulated and indeed the procedure itself can then be performed on a simple model.

It is an object of the present invention to provide a laparoscopic apparatus for the training of medical professionals, particularly those engaged in the field of laparoscopic surgery. In particular, it is envisaged that the present invention will provide a realistic surgical experience by mimicking the sensation of carrying out surgical techniques on a patient.

SUMMARY OF THE INVENTION

According to a first aspect of the present invention, there is provided a laparoscopic apparatus comprising a housing; a joint in operative association with the housing and adapted to substantially accommodate a laparoscopic tool, in use, through the joint, the joint permitting movement of the laparoscopic tool, in use; and resistance means in operative association with the joint, adapted to provide resistance to movement of the laparoscopic tool, in use.

Preferably, the housing comprises a base and a lid.

Preferably, the lid is generally curved in form, to substantially mimic the form of a human torso.

Preferably, the laparoscopic tool is a visual acquisition device.

Preferably, the joint further comprises a substantially hollow generally cylindrical tube, which is open at both ends.

Preferably, the joint permits concurrent movement of the laparoscopic tool (for example, the visual acquisition device) in all three axes. Further preferably, the joint is a rotatable joint.

Preferably, the joint is adapted to simulate the resistive forces experienced during laparoscopic surgical techniques.

Preferably, the joint comprises a ball-and-socket joint. The joint may comprise a ball rotatably engagable within a socket Preferably, the joint comprises a ball, and a socket within which the ball is at least partially housed; the ball being rotatably engagable within the socket, and the socket being adapted to provide resistance to movement of the ball.

Preferably, the socket is generally annular in form, and shaped and dimensioned to accommodate the ball therein.

Preferably, the ball is generally conoid. Although, it will be seen that the ball can be any form that permits triaxial rotation within the socket.

Preferably, the socket comprises a first section and a second section, spaced apart, shaped and dimensioned to house the ball therebetween. Optionally, the socket comprises a first section, and a second section spaced apart by a distance from the first section; the socket being shaped and dimensioned to house the ball therebetween.

Preferably, the first section can be removably mounted to the housing of the laparoscopic apparatus. Preferably, the first section is mounted by a plurality of clips.

Preferably, the first and second sections are biased towards one another by the resistance means. Alternatively, the first and second sections are biased away from one another by the resistance means. The resistance means may comprise at least one resiliently deformable resilient member. Preferably, the at least one resilient member extends between the first and second sections of the socket. Optionally, the resilient member is in operable association with one or both of the first and second sections of the socket. Further optionally, at least one of a respective terminal end of the resilient member is attached to one or both of the first and second sections.

Preferably, the resilient member is elastic.

Optionally, the resilient member comprises a spring. The spring may be, for example, a torsion spring, such as a coil spring or helical spring; or a flat spring, such as a leaf spring. The spring may be a compression spring or a tension spring. The coil or helical spring may be a compression coil or a tension coil.

Preferably, the distance between the first and second sections of the socket is defined by the spring in operable association with one or both of the first and second sections.

Preferably, the spring extends between the first and second sections.

Preferably, the resistance is adjustable by altering the pressure applied to the ball by the socket.

Preferably, the resistance is adjustable, by altering the distance between the first and second sections of the socket.

Optionally, the resistance means further comprises means to adjust the distance between the first and second sections of the socket. The adjusting means can be in operable association with one or both of the first and second sections.

Preferably, the adjusting means further comprises at least one actuator, which facilitates the adjustment of the relative distance between the first and second sections.

Preferably, the at least one actuator is a screw fixing.

Preferably, the spring is loaded by a screw fixing.

Optionally, a buffer is provided between the first and second sections of the socket. Further optionally, a buffer is provided between the ball and at least one of the first and second sections. Preferably, the buffer is formed from a deformable material, such as rubber.

Optionally, the housing of the laparoscopic apparatus further comprises one or more apertures through each of which a laparoscopic tool can pass, in use; the aperture being overlaid by a membrane to at least partially resist the laparoscopic tool, when the laparoscopic tool is applied thereto. It will be appreciated that when there are several apertures, the respective laparoscopic tools can be the same or different.

Preferably, the membrane comprises a synthetic skin. Further preferably, the membrane comprises a pad.

Preferably, the pad is adapted to simulate the resistive forces experienced during laparoscopic surgical techniques.

Preferably, the pad comprises an outer membrane, and a core. Preferably, the outer membrane at least partially surrounds the surface of the core.

Preferably, the outer membrane is formed from at least one synthetic material selected from the group including, but not limited to: synthetic latex, natural latex, a silicone elastomer, and a hydrocarbon solvent.

Preferably, the synthetic material is inert.

Preferably, the hydrocarbon solvent is a medium evaporating hydrocarbon solvent.

Preferably, the core comprises at least one silicone elastomer.

Preferably, the silicone elastomer is a pourable room temperature vulcanizing silicone rubber. Further preferably, it holds a Shore A Hardness of about 14.

Optionally, the core further comprises a liquid silicone elastomer.

Preferably, the pad is flexible. Optionally, it is extensible.

Optionally, the housing defines an internal chamber having a platform. Preferably, the position of the platform relative to the opening is adjustable.

Optionally, the laparoscopic apparatus further comprises a moveable platform. Preferably, the movable platform is located within the base of the laparoscopic apparatus.

Preferably, the platform comprises a first side and second side, the position of at least one of the first side and the second being adjustable relative to the opening.

Further preferably, the position of each side of the platform can be altered independently of any other side.

Optionally, a drawer is provided in the laparoscopic apparatus to accommodate instruments or any similar implements.

For the purposes of this specification, what is meant by the term "laparoscopic tool" is any instrument that may be used during the course of a laparoscopic operation, and is intended to include, but is not limited to cannulae, telescopes, and trocars.

BRIEF DESCRIPTION OF THE DRAWINGS

An embodiment of the invention will now be described, by way of example, with reference to the accompanying drawings, in which:

FIG. 6 is a cross-sectional side view of the rotatable joint of FIG. 4 in use;

DETAILED DESCRIPTION OF THE INVENTION

Figure 1:
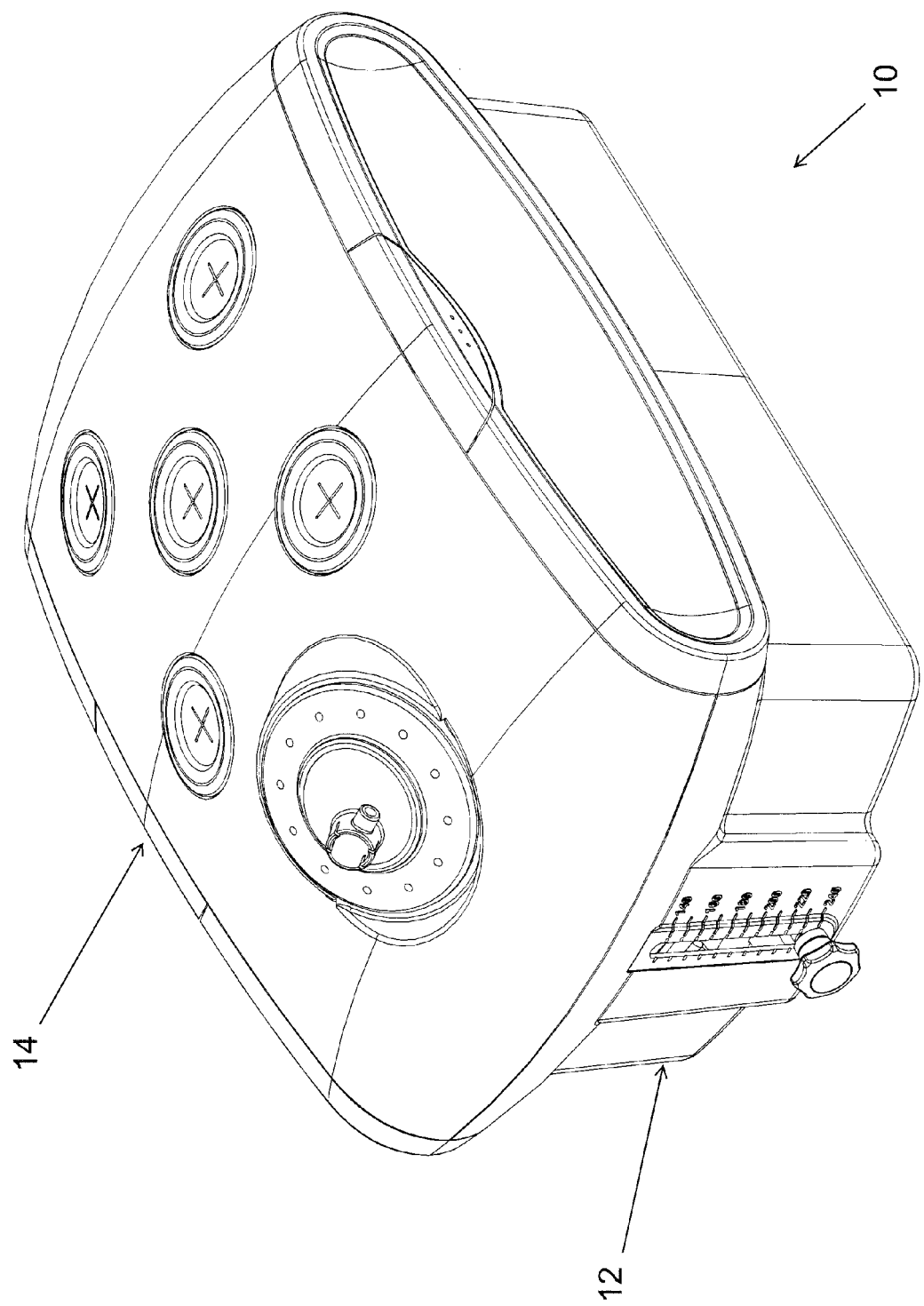
FIG. 1 is a perspective view of a laparoscopic apparatus according to a preferred embodiment of the present invention.

Referring now to FIG. 1 of the drawings, there is shown a laparoscopic apparatus 10 according to a preferred embodiment of the present invention. The laparoscopic apparatus 10 comprises a base section 12, and a lid section 14.

Figure 2:
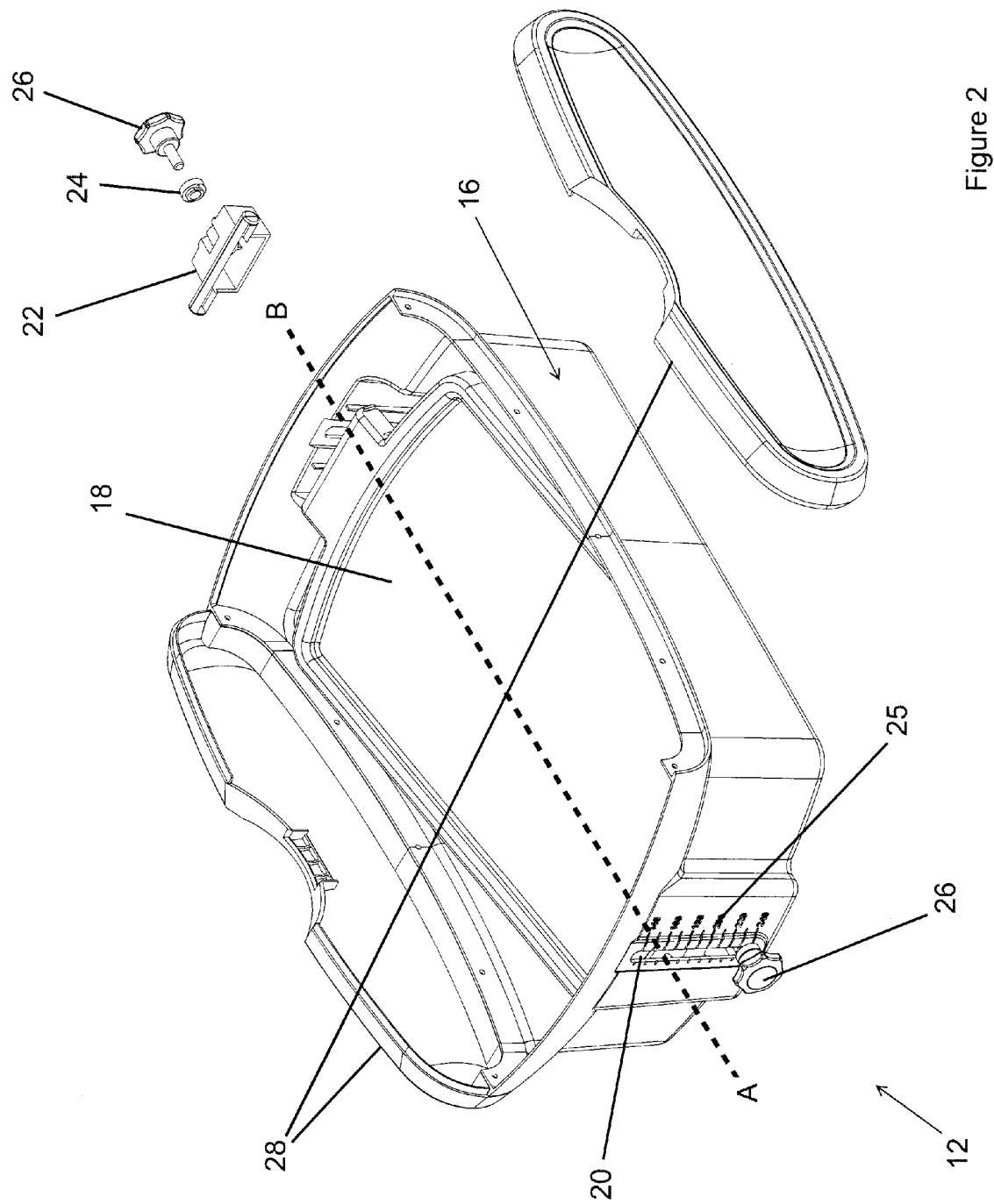
FIG. 2 is an exploded perspective view of a base section of the laparoscopic apparatus of FIG. 1.
Figure 3:
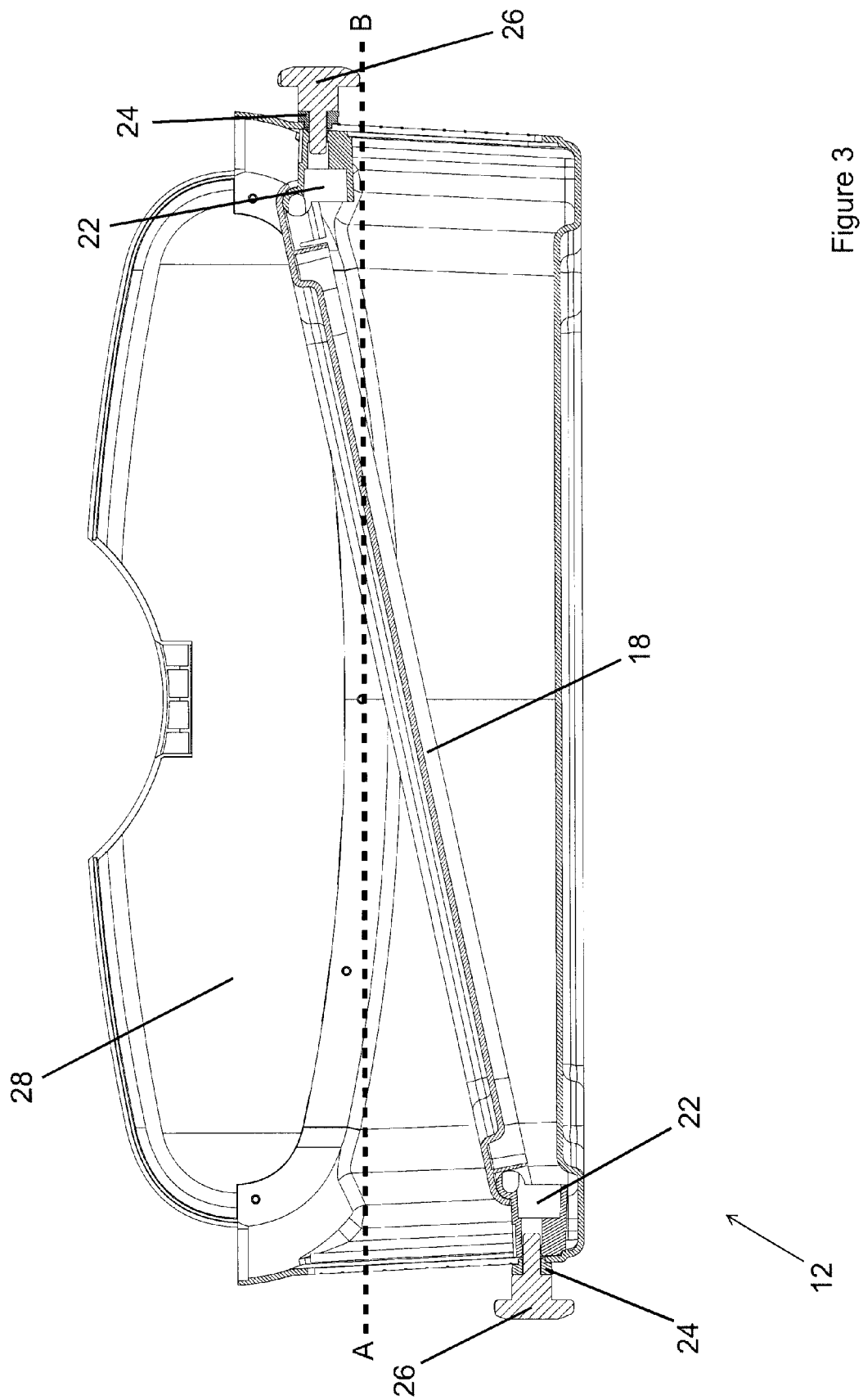
FIG. 3 is a cross-sectional side view along the line A-B of FIG. 2.

FIG. 2 is an exploded perspective view of the base section 12 of the laparoscopic apparatus 10. The base section 12 comprises a hollow substantially parallelepiped-shaped body 16, with an open, in use, uppermost face. A generally planar platform 18 is located within the body 16, and is of similar size to a, in use, bottom face of the body 16. A generally obround-shaped elongate aperture 20 is provided on at least one face of the body. Each elongate aperture 20 is substantially perpendicular to the longitudinal axis of the body 16. A hinge projection 22 is provided, which is cooperably attached to at least one side of the platform 18. The hinge projection 22 facilitates relative rotational motion between the platform 18 and the hinge projection 22. A screw threaded fixing bolt 26 is provided, which locates through the elongate aperture 20, and engages with the hinge projection 22 (See FIG. 3). An annular washer 24 is provided, which locates between the face of the body 16 and the fixing bolt 26, and engages with a numerical scale rule 25 to facilitate accurate quantitative placement of the hinge projection 22 relative to the elongate aperture 20. Adjusting the position of the fixing bolt 26 relative to the elongate aperture 20 can thereby temporarily alter the relative height of the side of the platform 18. A generally planar elliptical-shaped mount 28 is provided on each of two respective opposing sides of the body 16, and each is substantially parallel to and continuous with the respective sides of the body 16.

Figure 4:
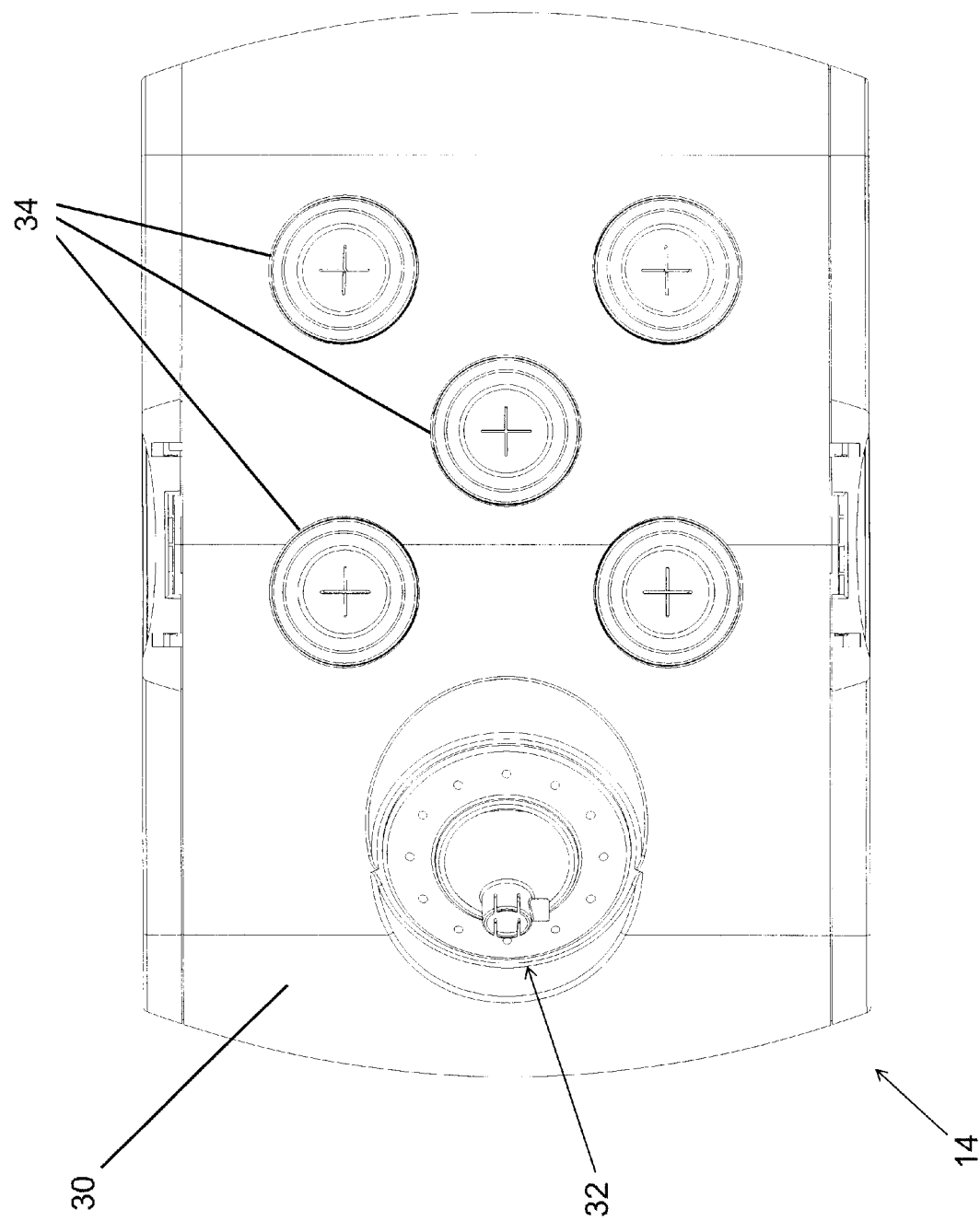
FIG. 4 is a plan view of a lid section of the laparoscopic apparatus of FIG. 1.

FIG. 4 is a plan view of the lid section 14 of the laparoscopic apparatus 10. The lid section 14 is generally rectangular in shape, and curved in form, FIG. 1. A number of apertures 34 are provided through the lid section 14. A joint 32 is provided through which, a laparoscopic tool 42, FIG. 6, can be mounted.

Figure 5:
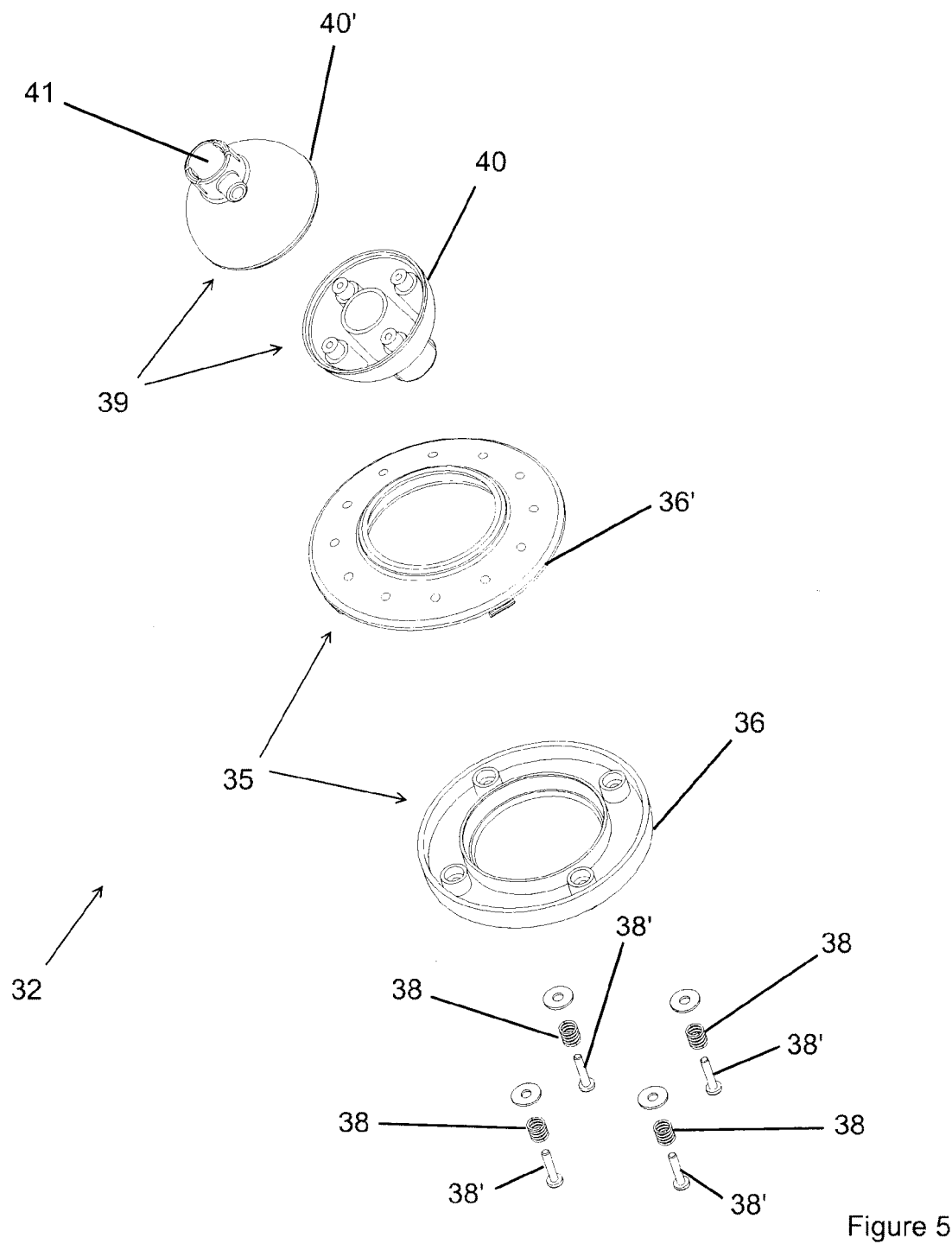
FIG. 5 is an exploded perspective view of a rotatable joint of the lid section of FIG. 4.

FIG. 5 is an exploded perspective view of the joint 32, which comprises a socket 35 and a ball 39. The socket 35 comprises an annular second section 36, which is inter-engaging with an annular first section 36'. The ball 39 comprises a generally hemi-spherical outer member 40' and a generally hemi-spherical inner member 40. A generally hollow cylindrical tube 41, is provided through each of the hemi-spherical members 40,40', and, in use, is substantially coaxial with the socket 35. When in use, the socket 35 inter-engages with the ball 39, facilitating rotation of the ball 39 through multiple planes relative to the socket 35.

In use, the first annular section 36' is spaced a distance apart from the second annular section 36, and the ball 39 is housed therebetween. The distance between the first annular section 36' and the second annular section 36 is defined by resistance means in the form of four springs 38. The springs 38 extend between each of the first annular section 36' and the second annular section 36. In an embodiment of the invention, the spring 38 is a compression spring, whereby the first annular section 36' and the second annular section 36 are biased away from each other. In an alternative embodiment, the spring 38 is a tension spring, whereby the first annular section 36' and the second annular section 36 are biased toward each other. In either case, the respective terminal ends of the spring 38 can be attached to one or both of the first annular section 36' and the second annular section 36.

It is, however, envisaged that the socket 35 may be formed from a resilient material, which can be adapted to apply varying pressure to the ball 39. In such an embodiment, the socket 35 is the resistance means.

Four screws 38' are provided, in use, to adjust the pressure applied to the ball 39 by the socket 35, and in the preferred embodiment illustrated, by adjusting the distance between the first annular section 36' and the second annular section 36. Each screw 38' extends between the first annular section 36' and the second annular section 36, and is in operable association with either of the sections 36, 36'. The first annular section 36' is provided with a complementary screw thread (not shown), with which each of the screws 38' can reversible engage, in use. Rotation of the screw 38' in a first direction will advance the screw 38' toward the first annular section 36', thereby decreasing the distance between the first annular section 36' and the second annular section 36. Rotation of the screw 38' in a second, opposing direction will retract the screw 38' toward the first annular section 36', thereby increasing the distance between the first annular section 36' and the second annular section 36.

FIG. 6 is a cross-sectional side view of the joint 32, in use, with a laparoscopic tool 42 mounted thereto. The first section 36' of the socket 35 is attached to the lid section 14, FIG. 4, by a set of clips 37. The second section 36 of the socket 35 is attached to the first section 36' by four spring biased screws 38, 38', surrounding the hemi-spherical members 40,40' of the ball 39. The ball 39 is positioned between the first section 36' and the second section 36 of the socket 35. The spring biased screws 38, 38' allow the level of friction to be adjusted between the first section 36' and the second section 36 of the socket 35, resultantly adjusting the friction between the socket 35 and the ball 39. The laparoscopic tool 42 is a telescope comprising a camera 44, which is mounted within the telescope body. An optical connection 46 transmits visual graphics from the camera 44 to a visual display unit (not shown).

Figure 7A:
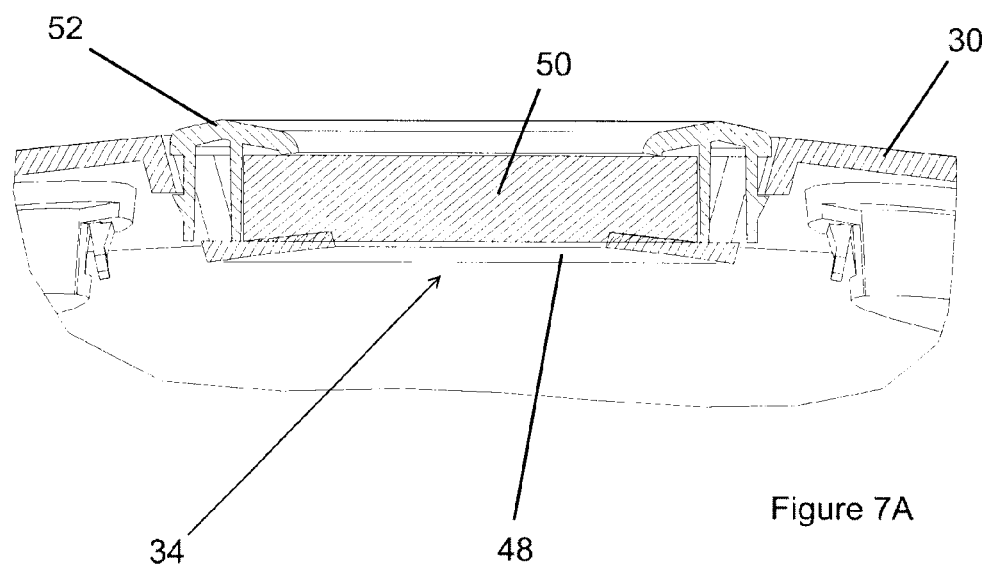
FIG. 7A is a cross-sectional view of an incision aperture of the lid of FIG. 4.
Figure 7B:
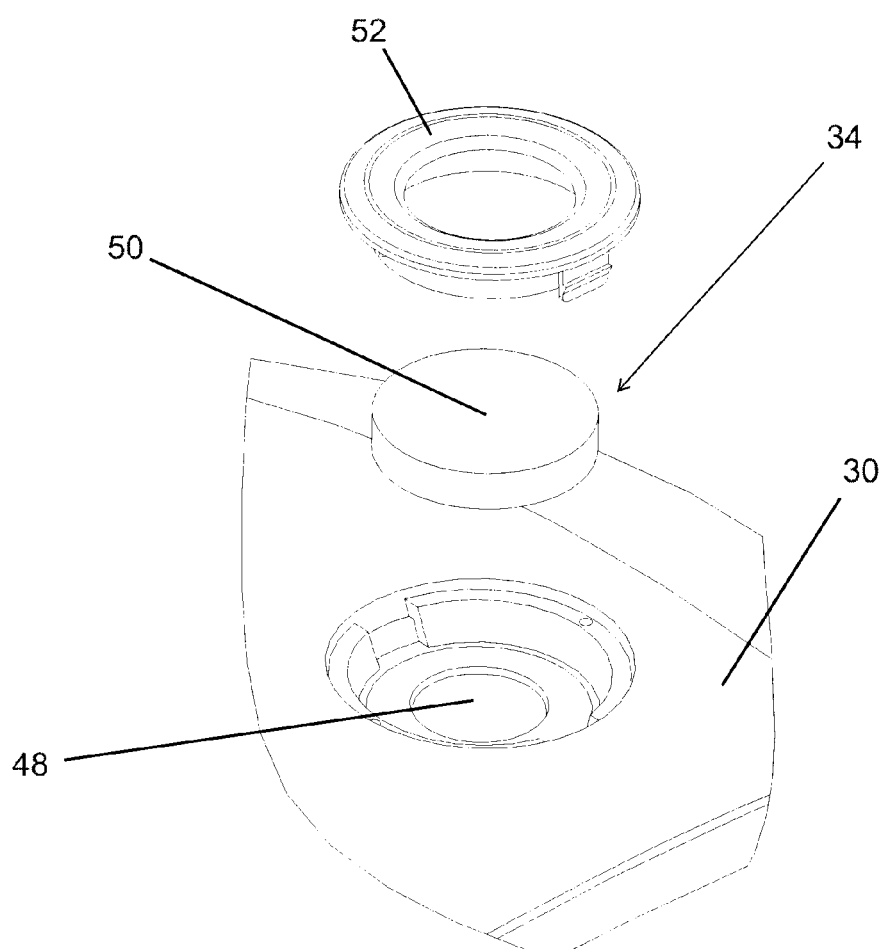
FIG. 7B is an exploded perspective view of an incision aperture of FIG. 7B.

FIG. 7A is a cross-sectional view of an aperture 34 of the lid section 14 of the laparoscopic apparatus 10. The aperture 34 comprises an annular housing 52 and a pad 50. The pad 50 is generally cylindrical in shape. The annular housing 52 is generally annular in form and is shaped and dimensioned to accommodate the pad 50, within the inner edge of the annular housing 52. The annular housing 52 locates in a recessed opening 48 in the housing 30 of the lid section 14 of the laparoscopic apparatus 10. Preferably, the pad 50 is formed from a material that is deformable under a first given pressure, but is severable under a second higher given pressure, so as to provide a realistic response representative of skin, when an instrument is applied with force against the pad 50.

The present invention finds utility in the training of medical professionals, such as trainee surgeons. In particular, the present invention finds utility as an affordable and portable platform that effectively demonstrates or trains laparoscopic skills and techniques by providing a realistic physical experience with real-time interaction outside of the operating room. The present invention allows a trainee surgeon to master the skills required to compensate for the narrow field of view, limitation of work space, and the lack of depth sensation associated with this field of surgery. The shape and dimension of the apparatus offers a realistic semblance to the human torso; and the integrated adaptable joint allows for a variety of laparoscopic instruments, including canullae, trocars and telescopes, to be used in a realistic fashion to augment both basic and advanced laparoscopic experiences, and ultimately to develop the coordination, technique, and precision of the trainee surgeon. The incision pads also lend to the realistic experience by mimicking the response of human skin to the application of a surgical instrument. Use of the invention in cooperative association with a visual display system also affords the user the opportunity to become acquainted with visualizing a 3-dimensional operative field as a 2-dimensional output, and the imposition associated therewith. Moreover, the simple and lightweight design makes the apparatus easy to assemble and transport. Taken together, the present invention provides a realistic surgical experience, by simulating the response of an actual human torso, without endangering patients or animal models.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A laparoscopic apparatus comprising:
    a housing;
    a joint in operative association with the housing and sized to substantially accommodate a laparoscopic tool, the joint comprising a ball rotatably engageable within a socket; and one or more resilient members adding resistance against movement of the joint.

2. A laparoscopic apparatus as claimed in claim 1, wherein the socket comprises a first section, and a second section spaced apart by a distance from the first section; the socket being shaped and dimensioned to at least partially house the ball therebetween.

3. A laparoscopic apparatus as claimed in claim 2, wherein the one or more resilient members are adjustable, by altering the distance between the first and second sections of the socket.

4. A laparoscopic apparatus as claimed in claim 3, wherein the distance between the first and second sections of the socket is defined by the one or more resilient members extending between the first and second sections.

5. A laparoscopic apparatus as claimed in claim 4, wherein the first and second sections of the socket are biased away from one another by the one or more resilient members.

6. A laparoscopic apparatus as claimed in claim 4, wherein the distance between the first and second sections of the socket is adjusted by an actuator in operable association with at least one of the first and second sections.

7. A laparoscopic apparatus as claimed in claim 5, wherein the one or more resilient members are one or more springs.

8. A laparoscopic apparatus as claimed in claim 6, wherein the actuator is a screw fixing.

9. A laparoscopic apparatus as claimed in claim 8, wherein rotation of the screw in a first direction advances the first section toward the second section.

10. A laparoscopic apparatus as claimed in claim 8, wherein rotation of the screw in a second, opposing direction retracts the first section from the second section.

11. A laparoscopic apparatus as claimed in claim 1, wherein the housing defines an internal chamber having a platform, the position of the platform relative to the joint being adjustable.

12. A laparoscopic apparatus as claimed in claim 11, wherein the platform comprises a first side and second side, the position of at least one of the first side and the second side being adjustable relative to the joint.

13. A laparoscopic apparatus as claimed in claim 1, wherein the housing defines at least one aperture, the aperture being overlaid by a membrane.

14. A laparoscopic apparatus as claimed in claim 13, wherein the membrane comprises a synthetic skin.

15. A laparoscopic apparatus as claimed in claim 5, wherein the distance between the first and second sections of the socket is adjusted by an actuator in operable association with at least one of the first and second sections.

* * * * *